United States Patent [19]

Thelen et al.

[11] 4,064,147

[45] Dec. 20, 1977

[54] PROCESS FOR THE PRODUCTION OF AROMATIC MONONITRO COMPOUNDS

[75] Inventors: Bernd Thelen, Leverkusen; Wolfgang Auge; Karl-Werner Thiem, both of Cologne, all of Germany

[73] Assignee: Bayer Aktiengesellschaft, Leverkusen, Germany

[21] Appl. No.: 685,467

[22] Filed: May 12, 1976

[30] Foreign Application Priority Data

May 16, 1975 Germany ............................ 2521891

[51] Int. Cl.$^2$ ..................... C07C 49/68; C07C 79/10; C07C 79/12
[52] U.S. Cl. .................................. 260/369; 260/645; 260/646
[58] Field of Search ...................... 260/369, 645, 646

[56] References Cited

U.S. PATENT DOCUMENTS

| 3,836,601 | 9/1974 | Frey et al. | 260/645 |
| 3,928,475 | 12/1975 | Dassel | 260/645 |
| 3,981,935 | 9/1976 | McCall | 260/645 |

*Primary Examiner*—Leland A. Sebastian
*Attorney, Agent, or Firm*—Burgess, Dinklage & Sprung

[57] ABSTRACT

Aromatic mononitro compounds are prepared by nitrating aromatic compounds with nitric acid having a concentration between 70 and 100% by weight, working up of the nitration mixture in a rectification column and separation of the aromatic mononitro compound.

In the nitration mixture and in the rectification column, depending upon the concentration of the nitric acid present, the ratio by weight of nitric acid plus water is controlled and not lowered below defined figures. Optionally water or nitric acid is introduced into the rectification column.

11 Claims, No Drawings

PROCESS FOR THE PRODUCTION OF AROMATIC MONONITRO COMPOUNDS

BACKGROUND

The present invention relates to a process for the production of aromatic mononitro compounds in which aromatic compounds are nitrated with nitric acid having a concentration between 70 and 100% by weight, working up of the nitration mixture by distillation and separation of the aromatic mononitro compounds.

It is known that certain aromatic mononitro compounds can be obtained by nitrating aromatic compounds with highly concentrated nitric acid. For example, it is known to produce 1-nitro anthraquinone from anthraquinone using nitric acid having a concentration of 85 to 100% by weight, to produce mononitro chlorobenzene from chlorobenzene with nitric acid having a density of 1.52 (this corresponds to nitric acid having a concentration of 98% by weight) to produce mononitro benzene from benzene using nitric acid having a concentration from 65 to 70% by weight. Thereby an excess of nitric acid is generally applied.

Because also nitro compounds having more than one nitro moiety in the molecule can be obtained in the nitration of aromatic compounds, the nitration mixture is normally diluted with a great amount of ice or water followed by isolation of the mononitro compound. Thereby the nitric acid is diluted to such a degree that it is not possible to reconcentrate it in an economic manner for a re-use in nitrations with highly concentrated nitric acid.

According to a recently developed process, a reaction mixture which contains 1-nitro anthraquinone and which is obtained by nitrating anthraquinone with highly concentrated nitric acid can be worked up by feeding the entire reaction mixture to an evaporator and rapidly distilling off a portion of the nitric acid (German Offenlegungsschrift(German Published Specification) 2,301,735). The advantage of this process is that the working up can be carried out in an uncomplicated apparatus. However, it is disadvantageous that the concentration of the nitric acid which is distilled off cannot be varied and that in the evaporator a great decrease in the ratio by weight of nitric acid to organic compounds takes place. When this ratio becomes too low special measures with reference to safety become necessary.

According to a further recently developed process for the nitration with nitric acid, especially for the nitration of anthraquinone, it can be effected in such a manner that first the nitration is terminated by the addition of diluted nitric acid followed by a separation of the reaction mixture into nitration product and two fractions of nitric acid having a different concentration (German Offenlegungsschrift(German Published Specification) 2,207,377). In this process the entire reaction mixture is first diluted followed by working up of the entire diluted nitric acid. It is a disadvantage of this process that great volumes of diluted nitric acid are to be worked up by distillation resulting in a more concentrated and a less concentrated fraction.

With reference to nitrations of other aromatic compounds than anthraquinone with highly concentrated nitric acid and the working up of such nitration mixtures only few references are available. Such compounds, for example benzene, toluene, napthalene, chlorobenzene, dichlorobenzene and similar compounds, are generally nitrated with mixed acids or with nitric acid having a lower concentration. However, the working up of mixed acids in order to bring them in a condition suitable for reusing is difficult and complicated. There is a prejudice against of highly concentrated nitric acid for the nitration of such compounds because it is known that in a plant for the nitration of benzene with nitric acid having a concentration between 65 and 70% a mixture of nitrobenzene, nitric acid and water detonated (Chem. Eng. May 9, 1966, p. 163 and Chem. Eng. News Nov. 28, 1960, p. 47).

SUMMARY

There has now been found a process for the production of aromatic mononitro compounds by nitrating aromatic compounds with nitric acid having a concentration between 70 and 100% by weight, working up of the nitration mixture by distillation and separation of the aromatic nitro compounds, which is characterized in that, in the nitration mixture, depending upon the concentration of the nitric acid present, the ratio by weight of nitric acid plus water to organic components is not below 3 (when nitric acid having a concentration of 70% by weight is present) or below 8 (when nitric acid having a concentration of 100% by weight is present) and that the nitration mixture is worked up in a rectification column, whereby in a said rectification column, depending upon the concentration of the nitric acid present, the ratios by weight of nitric acid plus water to organic components are not lowered between below 3 (when nitric acid having a concentration of 70% by weight and aromatic compounds having 1 aromatic nucleus respectively when nitric acid having a concentration of 78% by weight and aromatic compounds having more than one aromatic nucleus are present) and 8 (when nitric acid having a concentration of 100% by weight and aromatic compounds having one or more aromatic nucleus are present) whereby the nitration mixture is fed in the rectification part of said rectification column, whereby at the top of said rectification column a more concentrated nitric acid than in the nitration mixture is withdrawn and whereby in the sump of said rectification column a concentration of nitric acid between 66 and 70% by weight is maintained when nitration mixtures from the nitration of relatively reactive aromatic compounds are worked up and a concentration of nitric acid between 66 and 85% by weight is maintained when nitration mixtures from the nitration of relatively low reactive aromatic compounds are worked up, however, always a concentration of nitric acid lower than in the nitration mixture is maintained and whereby the aromatic mononitro compounds are separated out of the product discharged at the sump of the rectification column.

DESCRIPTION

According to the process of the invention, the nitration is carried out with nitric acid having a concentration between 70 and 100% by weight. It is preferred to nitrate relatively reactive aromatic compounds, for example benzene, toluene, naphthalene, chlorobenzene or dichlorobenzene, with nitric acid having a concentration between 70 and 90% by weight, especially with nitric acid having a concentration between 75 and 88% by weight. Less reactive aromatic compounds, for example anthraquinone, are preferably nitrated with nitric acid having a concentration between 85 and 100% by weight, especially with a nitric acid having a concentration between 90 and 99.5% by weight.

According to the invention such amounts of nitric acid are used that during the nitration, depending upon the concentration of the nitric acid, the ratio by weight of nitric acid plus water to organic components is not lower than defined. The ratio by weight as employed herein is defined as follows: The weight of the nitric acid present, calculated as nitric acid having a concentration of 100%, is added to the weight of the water present, brought in with the nitric acid and/or formed during the nitration, and this sum is divided by the total weight of the organic components present. The organic components present are mainly the introduced or unreacted aromatic compound and the nitration products of the aromatic compound.

When nitric acid with a concentration of 70% by weight is present in the nitration mixture, the ratio by weight should not be lower than 3, and when nitric acid with a concentration of 100% by weight is present, the ratio by weight should not be lower than 8. Between these two concentrations of nitric acid, in a first approximation, the limit of the ratio by weight which is not to be passed is dependent on the concentration of the nitric acid in a linear manner. When this dependency is considered more exactly, it is not strictly linear. At higher concentrations of nitric acid said dependency is more strongly marked than at lower concentrations of nitric acid.

Preferably, the process is carried out at higher ratios by weight than the above mentioned ratios by weight. For example, when nitric acid having a concentration of 70% is present the ratio by weight is not lower than 3.5, when nitric acid having a concentration of 100% is present the ratio by weight is not lower than 9 and when nitric acid of a concentration between these two values is present the ratio by weight is not lower than the corresponding intermediate values. Therefore, it is not absolutely necessary to know the small deviation from the linearity in the dependency between the concentration of the nitric acid and the ratio by weight which should not be lower than a distinct value.

The nitration according to the invention can be carried out at usual temperatures, for example at temperatures between 0° and 80° C. Preferably, the nitration is carried out at temperatures between 20° and 70° C. The nitration can be carried out in an adiabatic, partly adiabatic or isothermic manner.

The working up of the nitration mixture according to the invention is carried out in a rectification column. For this purpose any type of rectification column can be used, for example, a column containing trays or a packing or a trickling film column. Especially suitable are such rectification columns which are normally used for the preparation of highly concentrated nitric acid from a nitric acid having a concentration above 66% by weight. The rectification column is operated in a manner that nitric acid with a higher concentration than in the nitration mixture is withdrawn from the top. It is advantageous to withdraw at the top of the rectification column a nitric acid having such a concentration that the nitric acid can be reused for the nitration of the respective aromatic compound. It is further advantageous to reconcentrate the nitric acid, which becomes diluted during the nitration with water of reaction in such a manner that the concentration of the nitric acid withdrawn at the top of the rectification column corresponds to the concentration of the nitric acid which was originally introduced into the nitration. However, it is also possible to withdraw at the top of the rectification column a nitric acid having a higher concentration. The nitric acid withdrawn from the top of the rectification column can also contain nitrous oxides such as $N_2O_5$, $N_2O_4$, $NO_2$ and/or NO. When nitration mixtures from the nitration of relatively reactive aromatic compounds, for example from the nitration of benzene, toluene, naphthalene or chlorobenzene are worked up, it is preferred to withdraw from the top of the rectification column a nitric acid with a concentration between 75 and 88% by weight. When nitration mixtures from the nitration of relatively reactive aromatic compounds, for example anthraquinone, are worked up, it is preferred to withdraw from the top of the rectification column a nitric acid with a concentration between 90 and 99.5% by weight. The number of the plates in the rectification column to be used according to the invention depends on the concentration of the nitric acid in the nitration mixture which is introduced and from the desired concentration of the nitric acid to be withdrawn from the top. Generally, rectification columns can be used which have 1 to 20 theoretical plates. Preferably rectification columns are used which contain 2 to 15 theoretical plates.

The point at which the nitration mixture is introduced into the rectification column depends upon the concentration of the nitric acid in the nitration mixture and upon the concentration profile in the rectification column. When the nitric acid withdrawn from the top of the rectification column is to be reused for the same nitration, it is generally only necessary to effect a slight reconcentration of the nitric acid contained in the nitration mixture. In these cases the nitration mixture can be introduced into the rectification column on one of the upper plates, for example on the first or second plate below the top of the column. When a higher degree of reconcentration of the nitric acid contained in the nitration mixture is wanted, the introduction of the nitration mixture is advantageously effected at a lower point into the region of the rectification column where rectification takes place.

The rectification column is constructed and operated in a manner that in the sump a lower concentration of nitric acid than in the nitration mixture is present, however, the concentration of the nitric acid in the sump is not allowed to decrease below 66% by weight. When nitration mixtures from the nitration of relatively reactive aromatic compounds are worked up, for example nitration mixtures out of the nitration of benzene, toluene, chlorobenzene or naphthalene, the concentration of the nitric acid in the sump is maintained between 66 and 70% by weight. When nitration mixtures from the nitration of relatively less reactive aromatic compounds are worked up, for example nitration mixtures from the nitration of anthraquinone, the concentration of the nitric acid in the sump is maintained between 66 and 85% by weight, for example between 68 and 83% by weight, preferably between 70 and 80% by weight.

It is an essential aspect of the present invention that during the working up by distillation at all points of the rectification column, depending on the concentration of the nitric acid being present, the ratios by weight of nitric acid plus water to organic components are not lower than 3 (when nitric acid having a concentration of 70% by weight and aromatic compounds having 1 aromatic nucleus are present or when nitric acid having a concentration of 78% by weight and aromatic compounds having more than one aromatic nucleus are present) and not lower than 8 (when nitric acid having a concentration of 100% by weight and aromatic compounds having 1 or more aromatic nucleus are present). When nitric acid having a concentration below 78% by weight and aromatic compounds having more than one aromatic nucleus or nitric acid having a concentration below 70% by weight and aromatic compounds having one aromatic nucleus are present, the ratio by weight can be lower than 3.

It is not necessary to pay special attention to the part of the rectification column in which the reconcentration of the nitric acid takes place (this is the part between the introduction of the nitration mixture and the top of the rectification column). In this part of the rectification column higher ratios by weight are obtained than in the nitration mixture. Below the point where the nitration mixture is fed, especially in the sump of the column, the concentration of the organic compounds increases and, at the same time, the concentration of nitric acid decreases. Consequently, the ratio by weight is lowered in this part of the rectification column.

When the nitration mixture to be worked up contains a relatively low concentration of nitric acid, for example a nitric acid having a concentration between 70 and 90% by weight, and the ratio by weight is relatively high, for example, above 10 (when nitric acid having a concentration between 70 and 80% by weight is present) or above 15 (when nitric acid having a concentration between 80 and 90% by weight is present) it is possible that no special measures are necessary in order to avoid that the ratio by weight becomes too low in the lower part and in the sump of the rectification column. However, when other nitration mixtures are to be worked up, for example nitration mixtures containing nitric acid having a concentration between 70 and 85% by weight and wherein the ratio by weight is relatively low, for example below 10, or nitration mixtures in which the nitric acid is more concentrated, for example between 85 and 100% by weight and wherein the ratio by weight is below 15, it is generally necessary to adopt special measures to avoid that in the lower part and in the sump of the reaction column the ratios by weight do not decrease below the before mentioned figures. In these cases, it can be avoided that the ratio by weight becomes too low by introducing water or nitric acid having a concentration below the concentration of nitric acid in the nitration mixture below the point where the nitration mixture is fed in. Thereby it is to be regarded that water or nitric acid is added in such an amount that at no point of the rectification column the ratios by weight are lower than above stated. When nitric acid having a concentration above 66% by weight is added the maximum amount of the nitric acid to be added is not limited. When water or nitric acid having a concentration below 66% by weight is added, it is to be regarded that the concentration of nitric acid in the sump does not decrease below 66% by weight. The addition of water or nitric acid can be carried out at any point below the input of the nitration mixture, for example water or nitric acid can be introduced into the sump. When it is desired to effect the introduction into that part of the rectification column where rectification takes place, it is advantageous to add nitric acid with a concentration which differs not more than ± 5% by weight from the concentration of the nitric which is present at the point of introduction into the rectification column without the addition of said nitric acid. In this way the rectification in the column is not disturbed too much.

The rectification column can be operated at normal pressure, reduced pressure or slightly increased pressure independently of whether water or nitric acid is added or not. Generally, the rectification column is operated at pressures between 50 and 760 Torr preferably at pressures between 50 and 500 Torr. The temperatures at which the rectification column are operated depend upon the pressure in the rectification column, upon the concentration of the nitric acid being present in the nitration mixtures and upon the concentration of the nitric acid withdrawn at the top of the rectification column.

The reflux ratio (ratio of liquid feed back to withdrawn concentrated nitric acid) of the rectification column can be varied within wide limits. For example, the reflux ratio can be between 0 and 5. Reflux ratios between 0.1 and 1 are preferred. The concentration of the nitric acid which is optionally fed back can be higher than or equal to the concentration of nitric acid present on the plate on which the acid is fed back.

The separation of the aromatic mononitro compounds is effected out of the product discharged from the sump of the rectification column. When the aromatic mononitro compound is obtained in liquid form a separation between an aqueous, nitric acid containing phase and an organic, aromatic nitro compounds containing phase can be effected. For obtaining a better separation of the phases it can be advantageous to effect a cooling, for example a cooling to room temperature, before the separation of the phases is effected. It can be further advantageous to wash the organic phase after its separation from the aqueous phase one or more times, for example with water and/or an alkaline aqueous solution and/or a suitable organic solvent. When the aromatic mononitro compound is obtained in solid form, the separation can be effected by a mechanical separation, for example by a filtration, centrifugation or decantation. For obtaining the aromatic mononitro compounds in a higher yield it can be advantageous to cool and/or to further dilute the product discharged from the sump of the rectification column.

A separation of the aromatic mononitro compounds can be further effected by distilling off most of the nitric acid or all of the nitric acid, optionally in an apparatus where rectification can take place. Such a distillation can be effected with mixtures containing nitric acid having a concentration below 70% by weight and aromatic compounds having one aromatic nucleus or containing nitric acid having a concentration below 78% by weight and aromatic compounds having more than one aromatic nucleus. When the mixture withdrawn from the sump of the rectification column contains nitric acid having a higher concentration, it is necessary to dilute this mixture for obtaining a mixture suitable for such a distillation.

When the inventive process is applied to the production of 1-nitro anthraquinone by nitrating anthraquinone with nitric acid having a concentration between 85 and 100% by weight, working up of the nitration mixture by distillation and separation of 1-nitro anthraquinone by mechanical separation, the process can be carried out in such a manner that in the nitration mixture, depending upon the concentration of nitric acid being present, the ratio by weight of nitric acid plus water to organic components is not lower than 5 (when nitric acid having a concentration of 85% by weight is present) and 8 (when nitric acid having a concentration of 100% by weight is present) and, that the nitration mixture is worked up in a rectification column, whereby in said rectification column, depending on the concentration of the nitric acid being present, the ratio by weight is not lower than 3 (when nitric acid having a concentration of 78% by weight is present) and 8 (when nitric acid having a concentration of 100% is present), whereby the nitration mixture is introduced into the part of the rectification column where rectification takes place, whereby at the top of said rectification column a nitric acid having a higher concentration than the nitric acid in the nitration mixture and a concentration between 90 and 100% by weight is withdrawn, whereby below the point where the nitration mixture is introduced water or nitric acid having a concentration below the concentration of nitric acid in the nitration mixture but not higher than 90% by weight is added, whereby in the sump a lower concentration of nitric acid than in the nitration mixture and between 66 and 85% by weight is set up and whereby 1-nitro anthraquinone is separated out of the product discharged at the sump of the rectification column.

When the inventive process is applied to the production of 1-nitro anthraquinone, a technical embodiment of the invention can be carried out in the following manner:

Anthraquinone is nitrated with nitric acid having a concentration between 90 and 99.5% by weight. Thereby nitric acid is used in such an amount that at the beginning of the nitration, the ratio by weight of nitric acid plus water to anthraquinone is at least between 8, when nitric acid having a concentration of 90% by weight is used, and 11, when a nitric acid having a concentration of 99.5% is used. The nitration is carried out at a temperature between 20° and 70° C. After between 80 and 98% of the introduced anthraquinone has been nitrated, the nitration mixture is introduced into the upper part of a rectification column which contains altogether 4 to 10 theoretical plates. The rectification column is operated at a pressure between 80 and 300 Torr. From the top of the column, nitric acid is withdrawn having the same concentration as used for the nitration or a higher concentration. The reflux ratio at the top of the column is set between 0.1 and 1. Care is taken that at no point of the rectification column (including the sump) the ratio by weight of nitric acid plus water to organic components is not lower than 3 (when nitric acid having a concentration of 77% by weight is present) and 9 (when nitric acid having a concentration of 99.5% by weight is present) by adding water or nitric acid having a concentration below 80% by weight into the sump of the rectification column or by adding nitric acid having a concentration between 70 and 90% by weight into the part of the rectification column where rectification takes place but below the point where the nitration mixture is added. The addition of water or nitric acid and the operation of the rectification column is so regulated that in the sump a concentration of nitric acid between 70 and 85% by weight is set up, but at least a 10% (absolute) lower concentration of nitric acid than in the nitration mixture. The product discharged from the sump of the rectification column is cooled to 20° to 40° C and 1-nitro anthraquinone is separated by filtration or centrifugation. Before or after the cooling step, a dilution can be effected with nitric acid, for example with nitric acid having a concentration between 20 and 70% by weight, or with water.

When the inventive process is applied to the production of mononitro benzene, mononitro toluene, mononitro chlorobenzene, mononitro dichlorbenzene or mononitro naphthalene by nitration of benzene, toluene, chlorobenzene, dichlorobenzene or naphthalene the process can be carried out advantageously in a manner that the nitration is carried out in nitric acid having a concentration between 70 and 100% by weight, depending upon the concentration of the nitric acid being present during the nitration, the ratio by weight of nitric plus water to organic components is not lower than 3 (when nitric acid having a concentration of 70% by weight is present) and 10 (when nitric acid having a concentration of 100% by weight is present), that the nitration mixture is introduced into the rectification part of a rectification column which contains altogether 1 to 20 theoretical plates, in which the ratio by weight of nitric acid plus water to organic components is not lower than the values given above for the nitration, at the top of which a more concentrated nitric acid than in the nitration mixture is withdrawn and in the sump of which a concentration of nitric acid between 66 and 70% by weight but always a lower concentration of nitric acid than in the nitration mixture is set up, and from the product discharged at the sump mononitro benzene, mononitro toluene, mononitro chlorobenzene, mononitrodichlorobenzene or mononitro naphthalene is obtained, optionally after dilution and/or cooling by phase separation.

The inventive process has the following advantages: Special measures with reference to chemical engineering or safety can be avoided, though concentrated nitric acid can be present. The working up of the nitration mixture can be effected in a relatively uncomplicated rectification column, in which the termination of the nitration reaction and the setting up of suitable conditions for the separation of the aromatic mononitro compounds is reached. The amount of the required energy is lower than for the process according to German Offenlegungsschrift (German Published Specification) 2,220,377 because a nitric acid suitable for the nitration can be obtained directly from the nitration mixture without a preceding dilution. It is further advantageous that according to the inventive process relatively small volumes of nitric acid can be handled.

The aromatic mononitro compounds obtainable according to the process of the invention can be used as intermediates, for example, for the production of dyestuffs (see for example, Ullmann Encyclopaedia of Technical Chemistry, third Edition, volume 12 (1960), p. 773, 777 and 798). The following examples illustrate the inventive process without limitation.

EXAMPLES (the percentages are percentages by weight, if not stated otherwise)

EXAMPLE 1

In a mixing vessel 123.55 kg/h of nitric acid having a concentration of 95.5% and 11.18 kg/h of anthraquinone are mixed and dissolved continuously at 20° to 25° C with an average residence time of about 8 minutes. In the following tubular reactor the nitration is continued at 25° to 45° C with an average residence time of about 21 minutes in an adiabatic manner. The reaction mixture discharged from the reactor contains besides nitric acid having a concentration of 93.9% in dissolved form a mixture of 74.5 percent by weight 1-nitro-anthraquinone, 8.7 percent by weight of 2-nitro-anthraquinone, 9.5% by weight of dinitroanthraquinones and 6.9% by weight of anthraquinone. The reaction mixture is introduced on the third plate of a rectification column having 5 plates. At the top of the column 83.5 kg/h of nitric acid having a concentration of 99% is withdrawn, whereby a reflux ratio of 0.35:1 is maintained. Into the sump of the rectification column 31.69 kg/h of nitric acid having a concentration of 70% by weight is added. At the sump of the column 81.99 kg/h of a mixture is obtained, which shows a concentration of nitric acid of 77.5% and a ratio by weight of nitric acid + water to organic components of 5. The rectification column is operated at a pressure at the top of 200 Torr. The temperature at the top is 50° C. The temperature at the sump is 83° C. The product discharged from the sump is simultaneously cooled to 25° to 30° C and diluted with water or nitric acid having a concentration of 70%. After filtration 1-nitroanthraquinone is obtained in a purity of 90%.

EXAMPLE 2

In a vessel 20.80 kg/h of anthraquinone and 572.73 kg/h of nitric acid having a concentration of 88% are mixed at a temperature of 20° C. The nitration reaction is continued in a reaction cascade having four stages with an average residence time of 3 hours at a temperature of 60° to 65° C. The reaction mixture discharged from the reaction cascade contains nitric acid having a concentration of 86.5% and in dissolved form a mixture consisting of 76% 1-nitro-anthraquinone, 10% 2-nitroanthraquinone, 9% dinitroanthraquinones and 5% anthraquinone. The reaction mixture is introduced into a rectification column which contains 6 plates in the stripping section and 4 plates in the rectifying section. From the top of the rectification column 305.14 kg/h of nitric acid having a concentration of 99% are withdrawn. The reflux ratio is adjusted to 1:1. Out of the sump of the rectification column 263.04 kg/h of nitric acid and 25.38 kg/h organic components are withdrawn. In the sump of the rectification column the concentration of nitric acid is 72%. The column is operated at a pressure of 150 Torr at the top and at a temperature at the top of 42° C. The temperature in the sump is 86° C. 1-nitro-anthraquinone having a purity of 92% is obtained by cooling the product discharged from the sump to 20° to 30° C and filtration.

EXAMPLE 3

In a chamber reactor 20.80 kg/h of anthraquinone are continuously nitrated at 25° C with 205.71 kg/h nitric acid having a concentration of 98 to 99%. The average residence time is 15 minutes. The product discharged from the reactor has a concentration of nitric acid of 95.6% and contains in dissolved form a mixture of 78.8% 1-nitro-anthraquinone, 7.8% 2-nitro-anthraquinone, 6.3% dinitroanthraquinones and 6.1% anthraquinone. The reaction mixture is introduced on the third plate of a rectification column having 5 plates. At the top of the column 141.77 kg/h nitric acid having a concentration of 99% is withdrawn. The reflux ratio is adjusted to 0.25:1. Into the sump of the column 114.13 kg/h of nitric acid having a concentration of 70% are introduced. From the sump of the rectification column 173.67 kg/h nitric acid having a concentration of 76% and 25.24 kg/h of dissolved solids are withdrawn. The column is operated at the same conditions as stated in Example 1. After cooling to 25° to 30° C and filtration 1-nitroanthraquinone having a purity of 93 to 94% is obtained.

EXAMPLE 4

In a tubular reactor 20.80 kg/h of anthraquinone are continuously nitrated with 196.88 kg/h of nitric acid having a concentration of 96% at 50° C and an average residence time of 20 minutes. The product discharged from the reactor contains nitric acid having a concentration of 93.4% and in dissolved form a mixture of 73.6% 1-nitro-anthraquinone, 9.6% 2-nitro-anthraquinone, 9.5% dinitro-anthraquinones and 6.3% anthraquinone. The reaction mixture is introduced on the fourth plate of a rectification column containing 7 plates. From the top of the rectification column 128.37 kg/h of a nitric acid having a concentration of 99% are withdrawn. The reflux ratio is adjusted to 0.3:1. On the lowest plate of the rectification column 195.44 kg/h of nitric acid having a concentration of 70% are added. In the sump of the rectification column a concentration of nitric acid of 73% is maintained. From the sump 259.42 kg/h of nitric acid and additionally 25.35 kg/h dissolved products are withdrawn. The rectification column is operated at a pressure at the top of 150 Torr, at a temperature at the top of 42° C and at a temperature at the sump of 82° C. After cooling to 25° to 30° C and filtration 1-nitro-anthraquinone having a purity of 92% is obtained.

EXAMPLE 5

11.71 kg/h of anthraquinone are nitrated continuously with 132.72 kg/h nitric acid having a concentration of 94% in a tubular reactor at 45° C and an average residence time of 20 minutes. The reaction is carried out in an isothermal manner. The reaction mixture discharged during one hour from the reactor contains 14.29 kg/h of a crude nitro-anthraquinone and 130.13 kg/h nitric acid having a concentration of 93%. It is continuously fed to the third plate of a rectification column containing 5 plates. The column is operated at a pressure at the top of 200 Torr. From the top of the column 86.09 kg/h of nitric acid having a concentration of 98.5% are withdrawn. The reflux ratio is adjusted to 0.3:1. The temperature at the top is 50° C. Into the sump of the column 19.43 kg/h of a nitric acid having a concentration of 70% are added. From the sump of the column nitric acid having a concentration of 78.5% and 14.29 kg/h organic components are discharged at a temperature of 80° C. In the product discharged from the sump a concentration of nitric acid of 77% is maintained by adding a nitric acid having a concentration of 70%. After cooling to 25° to 30° C and filtration 1-nitroanthraquinone having a purity of 91% is obtained.

EXAMPLE 6

11.73 kg/h of anthraquinone are continuously nitrated with 186.78 kg/h nitric acid having a concentration of 98% at 10° C. The average residence time is 10 minutes. The reaction mixture discharged from the reactor during 1 hour contains 14.29 kg of a crude nitro-anthraquinone and 187,89 kg of nitric acid having a concentration of 97.5% and is fed on the top plate of a rectification column containing 6 plates. From the top of the column 86.29 kg/h of a nitric acid having a concentration of 99% are withdrawn. Into the sump of the column 26.05 kg/h of water are introduced. From the sump of the column a nitric acid having a concentration of 75% and 14.29 kg/h organic components are withdrawn. The temperature at the top of the column is 35° C, the sump temperature is 69° C and the pressure at the top is 100 Torr. After cooling of the product discharged from the sump to 25° to 30° C and filtration 1-nitroantraquinone having a purity of 94% is obtained.

EXAMPLE 7

In a continuous process 78 g of benzene and 785 g of nitric acid having a concentration of 80% are reacted in a tubular reactor under plug-flow conditions at a reaction temperature of 60° C and an average reaction time of 10 minutes. The reaction mixture is fed continuously in a rectification column containing one rectifying plate and 10 stripping plates. The column is operated at 50 Torr and a reflux ratio of 0.5:1 is adjusted. The temperature in the sump is 60° C and the temperature at the top is 39° C. From the sump of the rectification column per hour 497 g of a nitric acid having a concentration of 68% and 137 g organic components are discharged. From the top of the rectification column 375 g/h of a nitric acid having a concentration of 95% are discharged and recycled to the nitration. From the product discharged from the sump the acid phase is separated after cooling to 30° C by phase-separation. 39 g/h of the acid phase are separated out, the rest is recycled into the nitration. The organic phase is washed with water and than with a sodium carbonate solution of 2% strength. After drying in a falling film dryer 120 g/h of nitrobenzene having a purity of 99.8% are obtained (97.4% of theory).

What we claim is:

1. In a process for the production of aromatic compounds by nitrating aromatic compounds with nitric acid having a concentration between 70 and 100% by weight, working up of the nitration mixture by distillation and separation of the aromatic nitro compounds, the improvement which comprises, that in the nitration mixture, depending from the concentration of the nitric acid being present, the ratio by weight of nitric acid plus water to organic components is not lower than 3 (when nitric acid having a concentration of 70% by weight is present) and 8 (when nitric acid having a concentration of 100% by weight is present), that the nitration mixture is worked up in a rectification column, whereby in said rectification column the minimum value of the ratio by weight of nitric acid plus water to organic components are not lower than 3 (when nitric acid having a concentration of 70% by weight and aromatic compounds having 1 aromatic nucleus or when nitric acid having a concentration of 78% by weight and aromatic compounds having more than one aromatic nucleus are present) and 8 (when nitric acid having a concentration of 100% by weight and aromatic compounds having one or more aromatic nucleus are present), that the nitration mixture is fed into the rectification part of said rectification column, that at the top of said rectification column a more concentrated nitric acid than in the nitration mixture is withdrawn and that in the sump of said rectification column a concentration of nitric acid between 66 and 70% by weight is maintained when nitration mixtures from the nitration of relatively reactive aromatic compounds are worked up and a concentration of nitric acid between 66 and 85% by weight is maintained when nitration mixtures from the nitration of relatively low reactive aromatic compounds are worked up, but a concentration of nitric acid lower than in the nitration mixture is always maintained, and that the aromatic mononitro compounds are separated out of the product discharged at the sump of the rectification column.

2. A process according to claim 1, wherein the ratio by weight in the nitration mixture is not lower than 3.5 (when nitric acid having a concentration of 70% is present), not lower than 9 (when nitric acid having a concentration of 100% is present) and not lower than the corresponding intermediate values (when nitric acid of a concentration between 70 and 100% is present).

3. A process according to claim 1 wherein the nitration is carried out at temperatures between 0° and 80° C.

4. A process according to claim 1 wherein water or nitric acid having a concentration below the concentration of nitric acid in the nitration mixture is introduced into the rectification column below the point where the nitration mixture is fed in.

5. A process according to claim 4, wherein water or nitric acid is introduced into the sump.

6. A process according to claim 4, wherein nitric acid is introduced into that part of the rectification column, where rectification takes place, the nitric acid having a concentration which differs not more than ± 5% by weight from the concentration of the nitric acid which is present at the point of introduction into the rectification column without the addition of said nitric acid.

7. A process according to claim 1, wherein at the top of the rectification column a nitric acid is withdrawn having such a concentration that the nitric acid can be reused for the nitration of the respective aromatic compound.

8. A process according to claim 1, wherein a rectification column is used which has 1 to 20 theoretical plates.

9. A process according to claim 1, wherein the rectification column is operated at pressures between 50 and 760 torr.

10. In a process for the production of 1-nitro anthraquinone by nitrating anthraquinone with nitric acid having a concentration between 85 and 100% by weight, working up of the nitration mixture by distillation and separation of 1-nitro anthraquinone by mechanical separation, the improvements comprising that the process is carried out in such a manner that in the nitration mixture, depending upon the concentration of nitric acid being present, the ratio by weight of nitric acid plus water to organic components is not lower than 5 (when nitric acid having a concentration of 85% by weight is present) and 8 (when nitric acid having a concentration of 100% by weight is present) and, that the nitration mixture is worked up in a rectification column, that in said rectification column, depending on the concentration of the nitric acid present, the ratio by weight is not below 3 (when nitric acid having a concentration of 78% by weight is present) and 8 (when nitric acid having a concentration of 100% is present), that the nitration mixture is introduced into the part of the rectification column where rectification takes place, that at the top of said rectification column a nitric acid having a higher concentration than the nitric acid in the nitration mixture and a concentration between 90 and 100% by weight is withdrawn, that below the point where the nitration mixture is introduced water or nitric acid having a concentration below the concentration of nitric acid in the nitration mixture but not higher than 90% by weight is added, that in the sump a lower concentration of nitric acid than in the nitration mixture and between 66 and 85% by weight is set up and that 1-nitro anthraquinone is separated out of the product discharged at the sump of the rectification column.

11. In the production of mononitro benzene, mononitro toluene, chlorobenzene, mononitro dichlorobenzene or mononitro naphthalene by nitration of benzene, toluene, chlorobenzene, dichlorobenzene or naphthalene, the improvement comprising that the process is carried out in a manner that the nitration is carried out in nitric acid having a concentration between 70 and 100% by weight, depending upon the concentration of the nitric acid being present during the nitration, the ratio by weight of nitric acid plus water to organic components is not lower than 3 (when nitric acid having a concentration of 70% by weight is present) and 10 (when nitric acid having a concentration of 100% by weight is present), that the nitration mixture is introduced into the rectification part of a rectification column which contains altogether 1 to 20 theoretical plates, in which the ratio by weight of nitric acid plus water to organic components is not below the values given above for the nitration, at the top of which a more concentrated nitric acid than in the nitration mixture is withdrawn and in the sump of which a concentration of nitric acid between 66 and 70% by weight but always a lower concentration of nitric acid than in the nitration mixture is set up, and from the product discharged at the sump mononitro benzene, mononitro toluene, mononitro chlorobenzene, mononitrodichlorobenzene or mononitro naphthalene is obtained, optionally after dilution and/or cooling by phase separation.

* * * * *